(12) United States Patent
Niehrs et al.

(10) Patent No.: US 7,138,508 B2
(45) Date of Patent: Nov. 21, 2006

(54) INHIBITOR PROTEIN OF THE WNT SIGNAL PATHWAY

(75) Inventors: Christof Niehrs, Heidelberg (DE); Andrei Glinka, Heidelberg (DE)

(73) Assignee: Deutsches Krebsforschungszentrum Stiftung des Öffentlichen Rechts, Heidelberg (DE)

( * ) Notice: Subject to any disclaimer, the term of this patent is extended or adjusted under 35 U.S.C. 154(b) by 0 days.

(21) Appl. No.: 10/960,235

(22) Filed: Oct. 6, 2004

(65) Prior Publication Data

US 2005/0079173 A1   Apr. 14, 2005

Related U.S. Application Data

(63) Continuation of application No. 09/530,219, filed as application No. PCT/DE98/03155 on Oct. 27, 1998, now Pat. No. 6,844,422.

(30) Foreign Application Priority Data

Oct. 27, 1997   (DE) .................................. 197 47 418

(51) Int. Cl.
*C07K 14/00*   (2006.01)
*C07K 16/00*   (2006.01)

(52) U.S. Cl. ................ 536/23.1; 530/387.9; 530/388.1; 530/389.1; 530/350

(58) Field of Classification Search .................... None
See application file for complete search history.

(56) References Cited

OTHER PUBLICATIONS

Finch et al., Proc. Natl. Acad. Sci. USA, 1997, Jun. vol. 94, pp. 6770-6775.*

* cited by examiner

*Primary Examiner*—Gary B. Nukul
*Assistant Examiner*—Xiaozhen Xie
(74) *Attorney, Agent, or Firm*—Viola T. Kung; Howrey LLP

(57) ABSTRACT

The present invention relates to an inhibitor protein of the wnt signal path, a DNA encoding such a protein and a process for the preparation of such a protein. In addition, this invention concerns the use of the DNA and the protein as well as antibodies directed against the protein.

5 Claims, 11 Drawing Sheets

Fig. 2

Fig. 2 (Forts.)

Fig. 2 (Forts.)

Fig. 2 (Forts.)

Fig. 2 (Forts.)

Fig. 2 (Forts.)

```
                                                                                      phdkk-3
                                                                                      pcdkk-3
                                                                                      pmdkk-2
                                                                                      phdkk-2
                                                                                      pmdkk-1
                                                                                      plxfkk-1
                                                                                      pRNdkk-1

433  ........................................................................
 963  TCTGATTACGAAGAAAGCAGCGTCATTCAGGAAGTGCGTAAAGAATTAGAAAAGCCTGGAG
 798  TTATGTGCCTCATCTATGTAAATAATGTACACATTTGTGAAAATGCTATTATTAAAAGAA
 757  GTGAGGGTTAAT................................................
1030  CTGTGATTGCAgTAAATTACTGTGTTGTTGTAAATCCTCAgTGTGGCACTTACCTGTAAATGC
 829  ........................................................................
1061  TGTTGTAAATACTACGCAAGGAGACCTGTAAAAACTGTAAATACCCGTATAGAAAGTG phdkk-3
                                                                                      pcdkk-3
                                                                                      pmdkk-2
                                                                                      phdkk-2
                                                                                      pmdkk-1
                                                                                      phdkk-1
                                                                                      pRNdkk-1

433  ........................................................................
1023  GACCAAGCAGGTGTGAAGTCTGAGCATGACCCCGGCTCATGACCTATTTCTGGGAGATGAA
 858  AGCACCACCATGGAAATTACAAAAA...................................
 769  ........................................................................
1090  AgCAAAACTTTTAATTATTTTTCTAgAgGTGTGgTACATTGCCTTGTTTCTCTTGCATGT
 829  ........................................................................
1121  TACATGATCTTCTCTCTATTGTAACCTGCCACCTTGTACATTCCGACGCGCTCTTCCCTTTT phdkk-3
                                                                                      pcdkk-3
                                                                                      pmdkk-2
                                                                                      plxfkk-2
                                                                                      pmdkk-1
                                                                                      phdkk-1
                                                                                      pRNdkk-1

433  ........................................................................
1083  ATATGAAGTTCAAACACCAGTTTAGTTAGTCCTAGAAATTGTGTCTACTGTCTTGCTTA
 882  ........................................................................
 769  ........................................................................
1150  aAATTTTTTtGTaCACGGTTGATtGTCTTGAcTCATAAATATTCTATATTGgAgTagAA
 829  ........................................................................
1181  TATATATATATATATATATAAATATATATTATTATGTAGAGTTACGTCTAGTATGTCTG
```

Fig. 2 (Forts.)

```
                                                        plxdkk-3
                                                        pcdkk-3
                                                        pmdkk-2
                                                        plxdkk-2
                                                        pmdkk-1
                                                        plvdkk-1
                                                        pRNdkk-1

433   ........................................
1143  CATACACCCTTAAGAGATACTGCTGGATAGAAGTGCAATAAACATCTTCATTGAGCATCC
882   ........................................
769   ........................................
1210  AAAAAAAAAAAAAAAAA...........................
829   ........................................
1241  TATTTTTAATTGAAATAAAACATTCTAAACTTAAAAACAAAAAAAAAAAAAAAAA...

plxdkk-3
                                                        pcdkk-3
                                                        pmdkk-2
                                                        plxdkk-2
                                                        pmdkk-1
                                                        plvdkk-1
                                                        pRNdkk-1

433   ........................................
1203  GTTTTCGTGCACCAAACCTGCATGTTCAAATTCATGTTGAATTCACTCAATCTTTGGACC
882   ........................................
769   ........................................
1227  ........................................
829   ........................................
1298  ........................................

plxdkk-3
                                                        pcdkk-3
                                                        pmdkk-2
                                                        plxdkk-2
                                                        pmdkk-1
                                                        plvdkk-1
                                                        pRNdkk-1

433   ........................................
1263  AAACTTTCCATCAAAGACAAATGAGAAAGGCATCAGTGTTTCCTTTGGATTAATCCTTTC
882   ........................................
769   ........................................
1227  ........................................
829   ........................................
1298  ........................................
```

Fig. 2 (Forts.)

```
                                                         phdkk-3
                                                         pcdkk-3
                                                         pmdkk-2
                                                         phdkk-2
                                                         pmdkk-1
                                                         phdkk-1
                                                         pRNdkk-1

433    ....CTTTGTACAGCAGAAATAAACGTATCAGTACTCGTACTCATTAAAAAAACACACGGAGCA
1323   .................................................................
882    .................................................................
769    .................................................................
1227   .................................................................
829    .................................................................
1298   .................................................................

phdkk-3
                                                         pcdkk-3
                                                         pmdkk-2
                                                         phdkk-2
                                                         pmdkk-1
                                                         phdkk-1
                                                         pRNdkk-1

433    .
1383   T
882    .
769    .
1227   .
829    .
1298   .
```

Fig. 2 (Forts.)

SEQUENCE LISTING

<160> NUMBER OF SEQ ID NOS: 9

<210> SEQ ID NO 1
<211> LENGTH: 1297
<212> TYPE: DNA
<213> ORGANISM: Xenopus laevis

<400> SEQUENCE: 1

```
gacagtcgga gccggcgctg cagcatcaaa gggacttatc ttggaggact tgtgaattct      60
catcctgcca ttgtggttac tgagtctggt tggacagagg aatgggcagc aacatgttcc     120
cggtgcctct tattgtcttt tggggttta tcttggatgg ggcacttggc tttgtcatga      180
tgaccaactc caactccatc aagaatgtgc cggcggcacc agcaggtcag cccattggct     240
actaccctgt gagcgtcagt ccggactccc tatatgatat tgccaacaag taccaacctc     300
tggatgccta cccgctctac agttgcacgg aagatgatga ctgtgccctt gatgaattct     360
gtcacagttc cagaaacggc aactctctgg tttgcttggc atgccggaaa cgcagaaagc     420
gttgcctgag ggacgccatg tgctgcacag gcaactactg tagcaacgga atttgtgtcc     480
ctgtggagca agatcaagag cgcttccaac accagggata cctggaagaa accattctgg     540
aaaactataa taatgctgat catgcaacaa tggatactca ttccaaatta accacgtccc     600
catctggaat gcagcccttt aaaggccgtg atggtgatgt ttgcctccga tcaactgact     660
gtgcgccagg tctatgctgt gcccgtcatt tctggtcaaa gatctgcaag ccggtccttg     720
atgaaggcca agtgtgcacc aagcacagga ggaaaggctc tcacgggcta gagattttcc     780
agcgttgtca ctgcggtgcc ggactctcgt gccggttaca gaaaggagaa tttacaactg     840
tccctaaaac atcgagactt cacacttgcc aaagacacta agcgaggcct acagagcctg     900
aaggaccttc tctaaattaa gctaattaag actttggtac ctgcatgtta ttttctcagt     960
ttacatgaag tgctctggtc ttccctgaac ccggaagctg cgcaacttgt ttctttttt     1020 gaggaacttc ctaattaatg ctaattacag taaattactg tgttgtaaat actacgcaag    1080
gagacctgta aaaactgtaa atacccgtgt atagaaagtg tacatgatct tctctattgt    1140
aacctgccac cttgtacatt ccgacgcgct cttccctttt tatatatata tatatataaa    1200
```

| | |
|---|---|
| tatatattat attatgtaga gtttacgtct agtatgtctg tatttttaat tgaaataaaa | 1260 |
| catttctaaa cttaaaaaca aaaaaaaaaa aaaaaaa | 1297 |

<210> SEQ ID NO 2
<211> LENGTH: 881
<212> TYPE: DNA
<213> ORGANISM: Mus sp.

<400> SEQUENCE: 2

| | |
|---|---|
| tgcaggcatg aacaaggact gggttcggcg gcagtgagaa gggcaaaagc ctggggcagg | 60 |
| cctacccttg cagcagtgat aaggaatgtg aagttggaag atactgccac agtccccacc | 120 |
| aaggttcatc agcctgcatg ctctgtagga ggaaaaagaa acgatgccac agagatggga | 180 |
| tgtgttgccc tggtacccgc tgcaataatg gaatctgcat cccagtcact gagagcatcc | 240 |
| tcaccccaca tatcccagct ctggatggca cccggcatag gatcgcaac catggtcact | 300 |
| attccaacca tgacctggga tggcagaatc taggaaggcc acactccaag atgcctcata | 360 |
| taaaaggaca tgaaggagac ccatgcctac ggtcatcaga ctgcattgat gggttttgtt | 420 |
| gtgctcgcca cttctggacc aaaatctgca accagtgct ccatcagggg gaagtctgta | 480 |
| ccaaacaacg caagaagggt tcgcacgggc tggagatttt ccagaggtgt gactgtgcaa | 540 |
| agggcctgtc ctgcaaagtg tggaaagatg ccacctactc ttccaaagcc agactccatg | 600 |
| tatgccagaa gatctgataa acactggaag agtcatcact agcagactgt gaatttgtgt | 660 |
| atttaatgca ttatggcatg atggaaacct ggattggaat gcggaagaat gagggatgtg | 720 |
| gtaagaatgt ggagcagaag agggcaggac tgaatcaagt agagtcgaca acaaccaaag | 780 |
| tactaccagt gcttccgtta tgtgcctcat ctatgtaaat aatgtacaca tttgtgaaaa | 840 |
| tgctattatt aaaagaaagc acaccatgga aattacaaaa a | 881 |

<210> SEQ ID NO 3
<211> LENGTH: 1226
<212> TYPE: DNA
<213> ORGANISM: Mus sp.

<400> SEQUENCE: 3

| | |
|---|---|
| gacccacgcg tccgtgcctg tttgcgtcct tcggagatga tggttgtgtg tgcaccggca | 60 |
| gctgtccggt tcttggccgt gtttacaatg atggctctct gcagcctccc tctgctagga | 120 |
| gccagtgcca ccttgaactc agttctcatc aattccaacg cgatcaagaa cctgccccca | 180 |
| ccgctgggtg gtgctggggg gcagccgggc tctgctgtca gtgtgcgcc gggagttctc | 240 |
| tatgagggcg ggaacaagta ccagactctt gacaactacc agccctaccc ttgcgctgaa | 300 |
| gatgaggagt gcggctctga cgagtactgc tccagcccca gccgcggggc agccggcgtc | 360 |
| ggaggtgtac agatctgtct ggcttgccga aagcgcagga agcgctgcat gacgcacgct | 420 |
| atgtgctgcc ccgggaacta ctgcaaaaat ggaatatgca tgccctctga ccacagccat | 480 |
| tttcctcgag gggaaattga ggaaagcatc attgaaaacc ttggtaatga ccacaacgcc | 540 |
| gccgcggggg atggatatcc cagaagaacc acactgactt caaaaatata tcacaccaaa | 600 |
| ggacaagaag gctccgtctg cctccgatca tcagactgtg ccgcagggct gtgttgtgca | 660 |
| agacacttct ggtccaagat ctgtaaacct gtccttaaag aaggtcaggt gtgcaccaag | 720 |
| cacaaacgga aaggctccca cgggctggag atattccagc gctgttactg cggggaaggc | 780 |
| ctggcttgca ggatacagaa agatcaccat caagccagca attcttctag gctccacacc | 840 |
| tgccagagac actaaaccga cagtctaaat atgatggact ctttttatct aatatatgct | 900 |

| | |
|---|---:|
| acgaaaatcc tttatgattt gtcagctcaa tcccaaggat gtaggaatct tcagtgtgta | 960 |
| attaagcatt ccgacaatac tttccaaaag ctctggagtg taaggacttt gtttcttgat | 1020 |
| ggaactcccc tgtgattgca gtaaattact gtgttgtaaa tcctcagtgt ggcacttacc | 1080 |
| tgtaaatgca gcaaaacttt taattatttt tctagaggtg tggtacattg ccttgtttct | 1140 |
| cttgcatgta aatttttttt gtacacggtt gattgtcttg actcataaat attctatatt | 1200 |
| ggagtagaaa aaaaaaaaaa aaaaaa | 1226 |

<210> SEQ ID NO 4
<211> LENGTH: 768
<212> TYPE: DNA
<213> ORGANISM: Homo sapiens

<400> SEQUENCE: 4

| | |
|---|---:|
| atacgactca ctatagggaa tttggccctc gaggccaaga attcggcacg agggttggga | 60 |
| ggtattgcca cagtccccac caaggatcat cggcctgcat ggtgtgtcgg agaaaaaaga | 120 |
| agcgctgcca ccgagatggc atgtgctgcc ccagtacccg ctgcaataat ggcatctgta | 180 |
| tcccagttac tgaaagcatc ttaacccctc acatcccggc tctggatggt actcggcaca | 240 |
| gagatcgaaa ccacggtcat tactcaaacc atgacttggg atggcagaat ctaggaagac | 300 |
| cacacactaa gatgtcacat ataaaagggc atgaaggaga cccctgccta cgatcatcag | 360 |
| actgcattga agggttttgc tgtgctcgtc atttctggac caaaatctgc aaaccagtgc | 420 |
| tccatcaggg ggaagtctgt accaaacaac gcaagaaggg ttctcatggg ctggaaattt | 480 |
| tccagcgttg cgactgtgcg aagggcctgt cttgcaaagt atggaaagat gccacctact | 540 |
| cctccaaagc cagactccat gtgtgtcaga aatttgatca ccattgagg aacatcatca | 600 |
| attgcagact gtgaagttgt gtatttaatg cattatagca tggtggaaaa taaggttcag | 660 |
| atgcagaaga atggctaaaa taagaaacgt gataagaata tagatgatca caaaaaaaaa | 720 |
| aaaaaaaaag atgcggccgc aagcttattc cctttagtga gggttaat | 768 |

<210> SEQ ID NO 5
<211> LENGTH: 828
<212> TYPE: DNA
<213> ORGANISM: Homo sapiens

<400> SEQUENCE: 5

| | |
|---|---:|
| tggccccgca cgccaaaaat tcggcacgag ggtctggcac tcagaggatg ctctgacctt | 60 |
| gaaagggtcc tatctggaga cgagggagta caacgtgctg aatgtgtgcg gttcagggag | 120 |
| catttggtaa ccctgcattt gggagcagtg ggcactaacc ggttttggag aggtggacac | 180 |
| ataaggactg tgatcagcgc ccgggtccaa gagggcgggt acctggacct ctgggtgcct | 240 |
| caccctctcc ccgaaccctt cccacagccg taccgtgcg cagaggacga ggagtgcggc | 300 |
| actgatgagt actgcgctag tcccacccg cggagggac cgccggccgt gcaaatctgt | 360 |
| ctcgcctgca ggaagcgccg aaaacgctgc atgcgtcacg ctatgtgctg ccccgggaat | 420 |
| tactgcaaaa atggaatatg tgtgtcttct gatcaaaatc atttccgagg agaaattgag | 480 |
| gaaaccatca ctgaaagctt tggtaatgat catagcacct tggatgggta ttccagaaga | 540 |
| accaccttgt cttcaaaaat gtatcacacc aaaggacaag aaggttctgt ttgtctccgg | 600 |
| tcatcagact gtgcctcagg attgtgttgt gctagacact tctggtccaa gatctgtaaa | 660 |
| cctgtcctga agaaggtca agtgtgtacc aagcatagga gaaaaggctc tcatggacta | 720 |

| | |
|---|---:|
| gaaatattcc agcgttgtta ctgtggagaa ggtctgtctt gccggataca gaaagatcac | 780 |
| catcaagcca gtaattcttc taggcttcac acttgtcaga gacactaa | 828 |

<210> SEQ ID NO 6
<211> LENGTH: 432
<212> TYPE: DNA
<213> ORGANISM: Homo sapiens

<400> SEQUENCE: 6

| | |
|---|---:|
| gcggtggcgg ccgctctaga atagtggatc ccccgggctg caggaattcg gcacgagcgg | 60 |
| ctgcgggcgc agagcggaga tgcagcggct tggggccacc ctgctgtgcc tgctgctggc | 120 |
| ggcggcggtc cccacggccc ccgcgcccgc tccgacggcg acctcggctc cagtcaagcc | 180 |
| cggcccggct ctcagctacc gcaggagga ggccacctc aatgagatgt ccgcgaggt | 240 |
| tgaggaactg atggaggaca cgcagcacaa attgcgcagc gcggtggaag agatggaggc | 300 |
| agaagaagct gctgctaaag catcatcaga agtgaacctg gcaaacttac ctcccagcta | 360 |
| tcacaatgag accaacacag acacgaaggt tggaaataat accatccatg tgcaccgaga | 420 |
| aattcacaag tt | 432 |

<210> SEQ ID NO 7
<211> LENGTH: 1383
<212> TYPE: DNA
<213> ORGANISM: Gallus sp.

<400> SEQUENCE: 7

| | |
|---|---:|
| cggcgagcgg cagcggcggc tgaggagcgc cggggatgcg gcggggagag ggaccggcgc | 60 |
| cgcggcggcg atggctgctg ctgttggccg tgctggcggc tctgtgctgc gccgcggccg | 120 |
| ggagcggcgg gcggcggcga gcggccagcc tgggcgagat gctgcgggag gtggaggcgc | 180 |
| tgatggagga cacgcagcac aagctgcgca acgccgtgca ggagatggaa gctgaagaag | 240 |
| aaggggcaaa aaaactgtca gaagtaaaact ttgaaaactt acctcccacc taccataatg | 300 |
| agtccaacac agaaaccaga attggtaata aaactgttca gactcatcaa gaaattgata | 360 |
| aggttacaga taacagaact ggatcaacaa ttttttccga gacaattatt acatctataa | 420 |
| agggtggaga aaacaaaaga aatcatgagt gtatcattga tgaagactgt gaaacaggaa | 480 |
| agtattgcca gttctccacc tttgaataca gtgtcagcc ctgtaaaacc cagcatacac | 540 |
| actgctcacg agatgttgaa tgctgcggag accagctttg tgtttggggt gagtgcagga | 600 |
| aagccacttc aagaggagaa atggtacca tttgtgagaa ccaacatgac tgcaacccag | 660 |
| gaacgtgctg tgcttttcag aaagaactgc tgtttcctgt gtgcactccg ttacccgaag | 720 |
| aaggtgaacc ttgccatgat ccttcaaaca gacttctcaa cctgatcacc tgggaactgg | 780 |
| aacctgatgg agtactagag cgctgcccat gtgcaagtgg cttgatctgc aacctcaga | 840 |
| gcagccacag tactacatct gtgtgtgaac tgtcctccaa tgaaccagg aaaaacgaaa | 900 |
| agaagatcc cttgaacatg gatgagatgc catttatcag tttaataccc agagatattc | 960 |
| tttctgatta cgaagaaagc agcgtcattc aggaagtgcg taaagaatta gaaagcctgg | 1020 |
| aggaccaagc aggtgtgaag tctgagcatg acccggctca tgacctattt ctgggagatg | 1080 |
| aaatatgaag ttcaaacacc agtttagtta gtcctagaaa ttgttgtcta gtgtcttgct | 1140 |
| tacatacacc cttaacagat actgctggat agaagtgcaa taaacatctt cattgagcat | 1200 |
| ccgttttcgt gcaccaaacc tgcatgttca aattcatgtt gaattcactc aatctttgga | 1260 |
| ccaaactttc catcaaagac aaatgagaaa ggcatcagtg tttcctttgg attaatcctt | 1320 |

```
tcctttgtac agcagaaata aacgtatcag tactcgtact cattaaaaaa acacacggag    1380
cat                                                                 1383
```

<210> SEQ ID NO 8
<211> LENGTH: 44
<212> TYPE: PRT
<213> ORGANISM: Artificial Sequence
<220> FEATURE:
<223> OTHER INFORMATION: Description of Artificial Sequence: Consensus
      wnt Protein
<220> FEATURE:
<221> NAME/KEY: MOD_RES
<222> LOCATION: (2)..(8)
<223> OTHER INFORMATION: Any Amino Acid
<220> FEATURE:
<221> NAME/KEY: VARIANT
<222> LOCATION: (9)
<223> OTHER INFORMATION: Ay amino acid
<220> FEATURE:
<221> NAME/KEY: MOD_RES
<222> LOCATION: (10)..(16)
<223> OTHER INFORMATION: Any Amino Acid
<220> FEATURE:
<221> NAME/KEY: MOD_RES
<222> LOCATION: (18)..(19)
<223> OTHER INFORMATION: Any Amino Acid
<220> FEATURE:
<221> NAME/KEY: MOD_RES
<222> LOCATION: (21)..(26)
<223> OTHER INFORMATION: Any Amino Acid
<220> FEATURE:
<221> NAME/KEY: MOD_RES
<222> LOCATION: (28)..(32)
<223> OTHER INFORMATION: Any Amino Acid
<220> FEATURE:
<221> NAME/KEY: MOD_RES
<222> LOCATION: (35)..(38)
<223> OTHER INFORMATION: Any Amino Acid
<220> FEATURE:
<221> NAME/KEY: MOD_RES
<222> LOCATION: (40)..(41)
<223> OTHER INFORMATION: Any Amino Acid
<220> FEATURE:
<221> NAME/KEY: MOD_RES
<222> LOCATION: (43)
<223> OTHER INFORMATION: Any Amino Acid

<400> SEQUENCE: 8

Cys Xaa Xaa Xaa Xaa Xaa Xaa Xaa Xaa Xaa Xaa Xaa Xaa Xaa Xaa Xaa
  1               5                  10                  15

Cys Xaa Xaa Cys Xaa Xaa Xaa Xaa Xaa Xaa Cys Xaa Xaa Xaa Xaa Xaa
             20                  25                  30

Cys Cys Xaa Xaa Xaa Xaa Cys Xaa Xaa Gly Xaa Cys
         35                  40

<210> SEQ ID NO 9
<211> LENGTH: 65
<212> TYPE: PRT
<213> ORGANISM: Artificial Sequence
<220> FEATURE:
<223> OTHER INFORMATION: Description of Artificial Sequence: Consensus
      wnt Protein
<220> FEATURE:
<221> NAME/KEY: MOD_RES
<222> LOCATION: (2)..(3)
<223> OTHER INFORMATION: Any Amino Acid
<220> FEATURE:
<221> NAME/KEY: MOD_RES
<222> LOCATION: (5)..(6)
<223> OTHER INFORMATION: Any Amino Acid

```
<220> FEATURE:
<221> NAME/KEY: MOD_RES
<222> LOCATION: (8)..(11)
<223> OTHER INFORMATION: Any Amino Acid
<220> FEATURE:
<221> NAME/KEY: MOD_RES
<222> LOCATION: (14)..(15)
<223> OTHER INFORMATION: Any Amino Acid
<220> FEATURE:
<221> NAME/KEY: MOD_RES
<222> LOCATION: (17)
<223> OTHER INFORMATION: Any Amino Acid
<220> FEATURE:
<221> NAME/KEY: MOD_RES
<222> LOCATION: (21)..(24)
<223> OTHER INFORMATION: Any Amino Acid
<220> FEATURE:
<221> NAME/KEY: VARIANT
<222> LOCATION: (25)
<223> OTHER INFORMATION: Any amino acid
<220> FEATURE:
<221> NAME/KEY: MOD_RES
<222> LOCATION: (26)..(29)
<223> OTHER INFORMATION: Any Amino Acid
<220> FEATURE:
<221> NAME/KEY: MOD_RES
<222> LOCATION: (31)
<223> OTHER INFORMATION: Any Amino Acid
<220> FEATURE:
<221> NAME/KEY: MOD_RES
<222> LOCATION: (33)..(36)
<223> OTHER INFORMATION: Any Amino Acid
<220> FEATURE:
<221> NAME/KEY: MOD_RES
<222> LOCATION: (38)..(39)
<223> OTHER INFORMATION: Any Amino Acid
<220> FEATURE:
<221> NAME/KEY: MOD_RES
<222> LOCATION: (41)..(47)
<223> OTHER INFORMATION: Any Amino Acid
<220> FEATURE:
<221> NAME/KEY: VARIANT
<222> LOCATION: (48)
<223> OTHER INFORMATION: Any amino acid
<220> FEATURE:
<221> NAME/KEY: MOD_RES
<222> LOCATION: (49)..(55)
<223> OTHER INFORMATION: Any Amino Acid
<220> FEATURE:
<221> NAME/KEY: MOD_RES
<222> LOCATION: (58)
<223> OTHER INFORMATION: Any Amino Acid
<220> FEATURE:
<221> NAME/KEY: MOD_RES
<222> LOCATION: (60)..(61)
<223> OTHER INFORMATION: Any Amino Acid
<220> FEATURE:
<221> NAME/KEY: MOD_RES
<222> LOCATION: (64)
<223> OTHER INFORMATION: Any Amino Acid

<400> SEQUENCE: 9

Gly Xaa Xaa Gly Xaa Xaa Cys Xaa Xaa Xaa Xaa Asp Cys Xaa Xaa Gly
 1               5                  10                  15

Xaa Cys Cys Ala Xaa Xaa Xaa Xaa Xaa Xaa Xaa Xaa Xaa Cys Xaa Pro
                20                  25                  30

Xaa Xaa Xaa Xaa Gly Xaa Xaa Cys Xaa Xaa Xaa Xaa Xaa Xaa Xaa Xaa
            35                  40                  45

Xaa Xaa Xaa Xaa Xaa Xaa Xaa Arg Cys Xaa Cys Xaa Xaa Gly Leu Xaa
    50                  55                  60

Cys
 65
```

INHIBITOR PROTEIN OF THE WNT SIGNAL PATHWAY

PRIORITY INFORMATION

This application claims priority as a continuation application of U.S. patent application Ser. No. 09/530,219, filed Jul. 27, 2000, which is a National Stage of International Application PCT/DE98/03155, filed Oct. 27, 1998, published May 6, 1999 under PCT Article 2192) in German; which claims priority to German Patent Application No. 19747418.7, filed Oct. 27, 1997, each of which is incorporated by reference herein in its entirety.

SUMMARY OF THE INVENTION

The present invention relates to an inhibitor protein of the wnt signal path, a DNA encoding such a protein, and a process for preparing such a protein. Furthermore, this invention concerns the use of the DNA and the protein as well as antibodies directed against the protein.

The wnt signal path plays an important part for the regulation of cell proliferation and differentiation during the embryonal development of *Drosophila, Xenopus laevis* and mice. The wnt signal path comprises the combination of secretory glycoproteins encoded by wnt genes, e.g. Xwnt-8, and wnt receptors to which the glycoproteins bind. In addition, the wnt signal path in man is causally implied in the colon and mammary carcinomas as well as the melanomas (cf. Peifer, M., Science 275, (1997), 1752–1753). Therefore, inhibitors of the wnt signal path could represent a possibility of taking therapeutic against tumoral diseases.

Thus, it is the object of the present invention to provide a product by which the wnt signal path can be inhibited.

According to the invention this is achieved by the subject matters defined in the claims.

Therefore, the subject matter of the present invention relates to an inhibitor protein of the wnt signal path, the protein comprising at least one of the amino acid consensus sequences I (SEQ ID NO: 8) and II (SEQ ID NO: 9), indicated in FIG. 1.

The present invention is based on the applicant's finding that in animals, particularly mammals, very particularly human beings, there is exists a protein which inhibits the wnt signal path. The applicant has found that in *Xenopus laevis* the expression of the wnt gene, Xwnt-8, results in the formation of Siamese twins. This anomaly will be prevented if the above protein is expressed simultaneously. This protein is a secretory protein of about 40 kD. It has at least one of the amino acid consensus sequences I (SEQ ID NO: 8) and II (SEQ ID NO: 9) rich in cysteine and indicated in FIG. 1. Variants of the protein are indicated in the form of their DNAs in FIG. 2. The applicant has also found that variants of the protein are expressed in differing tissues (cf. Table 1 and FIG. 3).

The present invention refers to the above protein as "wnt inhibitor" (wnt-I).

In a preferred embodiment, (wnt-I) has the amino acid consensus sequences I (SEQ ID NO: 8) and II (SEQ ID NO: 9) indicated in FIG. 1.

A further subject matter of the invention relates to a nucleic acid coding for (wnt-I). It can be an RNA or a DNA. The latter may be a genomic DNA or a cDNA, for example. A DNA is preferred which comprises the following:

(a) the DNA of FIG. 2 or a DNA differing therefrom by one or several base pairs,
(b) a DNA hybridizing with the DNA of (a), or
(c) a DNA related to the DNA of (a) or (b) via the degenerated genetic code.

The expression "hybridizing DNA" refers to a DNA which hybridizes with a DNA of (a) under normal conditions, particularly at 20° C. below the melting point of the DNA.

The DNA of FIG. 2 comprises seven DNAs originating from *Xenopus laevis*, mice, human beings or chickens and coding for (wnt-I). Six of these DNAs were deposited with the DSMZ (Deutsche Sammlung von Mikroorganismen and Zellkulturen [German-type collection of micro-organisms and cell cultures]) on Sep. 19, 1997 as follows:

FIG. 2.1 (DNA from human beings, SEQ ID NO: 6) as phdkk-3 under DSM 11762
FIG. 2.2 (DNA from chickens, SEQ ID NO: 7) is termed pcdkk-3
FIG. 2.3 (DNA from mice, SEQ ID NO: 2) as pmdkk-2 under DSM 11759
FIG. 2.4 (DNA from human beings, SEQ ID NO: 4) as phdkk-2 under DSM 11761
FIG. 2.5 (DNA from mice, SEQ ID NO: 3) as pmdkk-1 under DSM 11758
FIG. 2.6 (DNA from human beings, SEQ ID NO: 5) as phdkk-1 under DSM 11760
FIG. 2.7 (DNA from *Xenopus laevis*, SEQ ID NO: 1) as pRNdkk-1 under DSM 11757.

A DNA according to the invention is described below in the form of a cDNA. It is exemplary for every DNA falling under the present invention.

For the preparation of a cDNA according to the invention it is favorable to use a *Xenopus laevis* cDNA library, as a basis (cf. Glinka, A. et al., Mechanisms Develope 60, (1996), 221–231). Corresponding mRNAs are synthesized from the individual cDNA clones by means of RNA polymerase. They are microinjected into *Xenopus laevis* together with mRNA of wnt genes, e.g. Xwnt-8. *Xenopus laevis* is screened for the development of Siamese twins. The latter are obtained when the mRNA of the wnt gene is microinjected as such or together with such a *Xenopus laevis* RNA which does not code for (wnt-I). Thus, the non-occurrence of Siamese twins is evaluated as an evidence for the presence of an mRNA coding for (wnt-I). Such an mRNA reveals directly the corresponding cDNA.

A cDNA according to the invention can be present in a vector and expression vector, respectively. A person skilled in the art is familiar with examples thereof. In the case of an expression vector for *E. coli* these are e.g. pGEMEX, pUC derivatives, pGEX-2T, pET3b and pQE-8. For the expression in yeast, e.g. pY100 and Ycpad1 have to be mentioned while e.g. pKCR, pEFBOS, cDM8 and pCEV4 have to be indicated for the expression in animal cells. The baculovirus expression vector pAcSGHisNT-A is especially suitable for the expression in insect cells.

The person skilled in the art knows suitable cells to express a cDNA according to the invention, which is present in an expression vector. Examples of such cells comprise the *E. coli* strains HB101, DH1, x1776, JM101, JM109, BL21 and SG 13009, the yeast strain *Saccharomyces cerevisiae* and the animal cells L, 3T3, FM3A, CHO, COS, Vero and HeLa as well as the insect cells sf9.

The person skilled in the art knows in which way a cDNA according to the invention has to be inserted in an expression vector. He is also familiar with the fact that this cDNA can be inserted in combination with a DNA coding for another protein and peptide, respectively, so that the cDNA according to the invention can be expressed in the form of a fusion protein.

Furthermore, the person skilled in the art knows conditions of culturing transformed cells and transfected cells, respectively. He is also familiar with processes of isolating and purifying the protein expressed by the cDNA according to the invention. Thus, such a protein, which may also be a fusion protein, also represents a subject matter of the present invention.

A further subject matter of the present invention relates to an antibody directed against an above protein and fusion protein, respectively. Such an antibody can be prepared by common methods. It may be polyclonal and monoclonal, respectively. For its preparation it is favorable to immunize animals—particularly rabbits or chickens for a polyclonal antibody and mice for a monoclonal antibody—with an above (fusion) protein or with fragments thereof. Further "boosters" of the animals may be effected with the same (fusion) protein or with fragments thereof. The polyclonal antibody may then be obtained from the animal serum and egg yolk, respectively. As regards the monoclonal antibody, animal spleen cells are fused with myeloma cells.

The present invention enables to better investigate and understand the wnt signal path. (wnt-I) can be detected in organisms by an antibody according to the invention. In addition, an autoantibody directed against this protein can be detected by a (wnt-I) according to the invention. Both detections can be made by common methods, particularly a Western blot, an ELISA, an immunoprecipitation or by immunofluorescence. Moreover, the expression of the gene coding for (wnt-I) can be detected by a nucleic acid according to the invention, particularly a DNA and primers derived therefrom. This detection can be made as usual, particularly in a Southern blot.

Thus, the present invention also serves for better investigating, i.e. diagnosing, and understanding processes which are connected with the wnt signal path. These are e.g. cell proliferation and differentiation as well as diseases of the most varying kinds. Examples of the latter are diseases of the eyes and bones as well as tumoral diseases, particularly colon and mammary carcinomas as well as melanomas.

Besides, the present invention is suitable to take measures for and against the presence of (wnt-I) in organisms. (wnt-I) can be inhibited in organisms by means of an antibody according to the invention. On the other hand, the amount of (wnt-I) in organisms can be increased by a (wnt-I) according to the invention, particularly after linkage to a protein which is not considered foreign by the body, e.g. transferrin or BSA. The same can also be achieved correspondingly by means of a nucleic acid according to the invention, particularly a DNA, which is controlled by a promoter inducible in certain tissues and which after its expression results in the provision of (wnt-I) in these tissues. In addition, a nucleic acid according to the invention, particularly a DNA, can also be used to inhibit (wnt-I). For this purpose, the nucleic acid is used e.g. as a basis for preparing anti-sense oligonucleotides for the expression inhibition of the gene coding for (wnt-I).

Thus, the present invention also provides the possibility of interfering with the wnt signal path in an activating fashion and inhibitory fashion, respectively. The former could be made e.g. by administration of an antibody according to the invention against (wnt-I). For the latter, it is an obvious thing to administer (wnt-I) according to the invention. The activation of the wnt signal path could be useful if it is considered to culture organisms for the purpose of organ donation. However, the inhibition of the wnt signal path offers itself so as to be able to take therapeutic steps in the case of diseases of bones and eyes as well as tumoral diseases, particularly colon and mammary carcinomas as well as melanomas.

In particular, the present invention distinguishes itself in that it can be used in tissue-specific fashion. This applies to both diagnosis and treatment. For example, a DNA according to the invention, Dkk-1 (SEQ ID NO: 1, SEQ ID NO: 3 or SEQ ID NO: 5), a corresponding protein and an antibody thereof, respectively, are particularly suitable for tissues, such as brain, heart, vessels, bones, cartilage, connective tissue and eye. Furthermore, a DNA according to the invention, Dkk-2 (SEQ ID NO: 2 or SEQ ID NO: 4), a corresponding protein and antibody thereof, respectively, are particularly suitable for tissues, such as brain, heart, vessels, bones, connective tissue, kidneys, testes, spleen, ovaries, muscles, uteri, cartilage, eyes and mammas. Moreover, a DNA according to the invention, Dkk-3 (SEQ ID NO: 6), a corresponding protein and an antibody thereof, respectively, are particularly suitable for tissues, such as brain, heart, vessels, bones, cartilage, eyes, connective tissue, lungs, ovaries, muscles and mammas.

BRIEF DESCRIPTION OF THE DRAWINGS

FIG. 2 shows the base sequence of seven DNAs coding for (wnt-I) by indicating the bases contributing to the amino acid consensus sequences of (wnt-I).

2.1, SEQ ID NO: 6
2.2, SEQ ID NO: 7
2.3, SEQ ID NO: 2
2.4, SEQ ID NO: 4
2.5, SEQ ID NO: 3
2.6, SEQ ID NO: 5
2.7, SEQ ID NO: 1.

Figure 1:
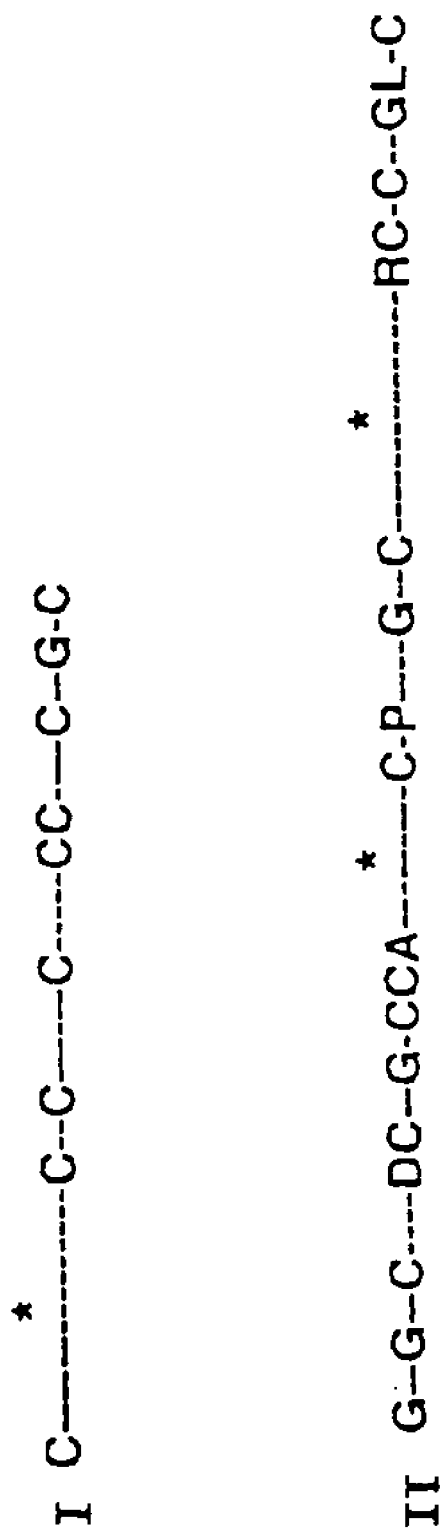
FIG. 1 shows the amino acid consensus sequences I (SEQ ID NO: 8) and II (SEQ ID NO: 9) of a (wnt-I) according to the invention. The indication "-" stands for an amino acid, the number of amino acids being variable when they are provided with an asterisk.
Figure 3:
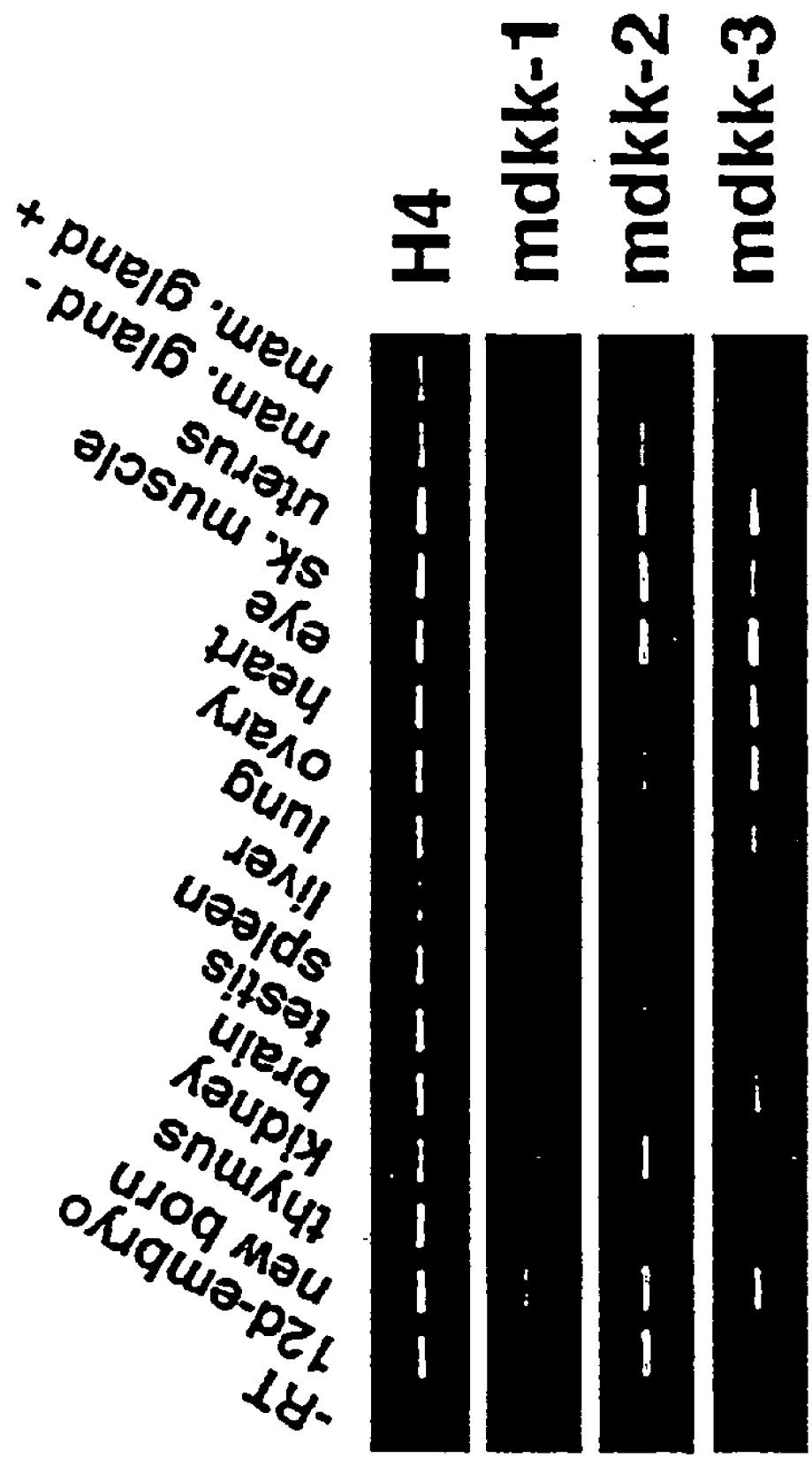

FIG. 3 shows the expression of three DNAs coding for (wnt-I), Dkk-1 (SEQ ID NO: 1), Dkk-2 (SEQ ID NO: 2) and Dkk-3 (SEQ ID NO: 6), in tissues.

EXAMPLES

The present invention is explained by the below examples.

Example 1

Preparation and Purification of a (wnt-I) According to the Invention

Figure 2:
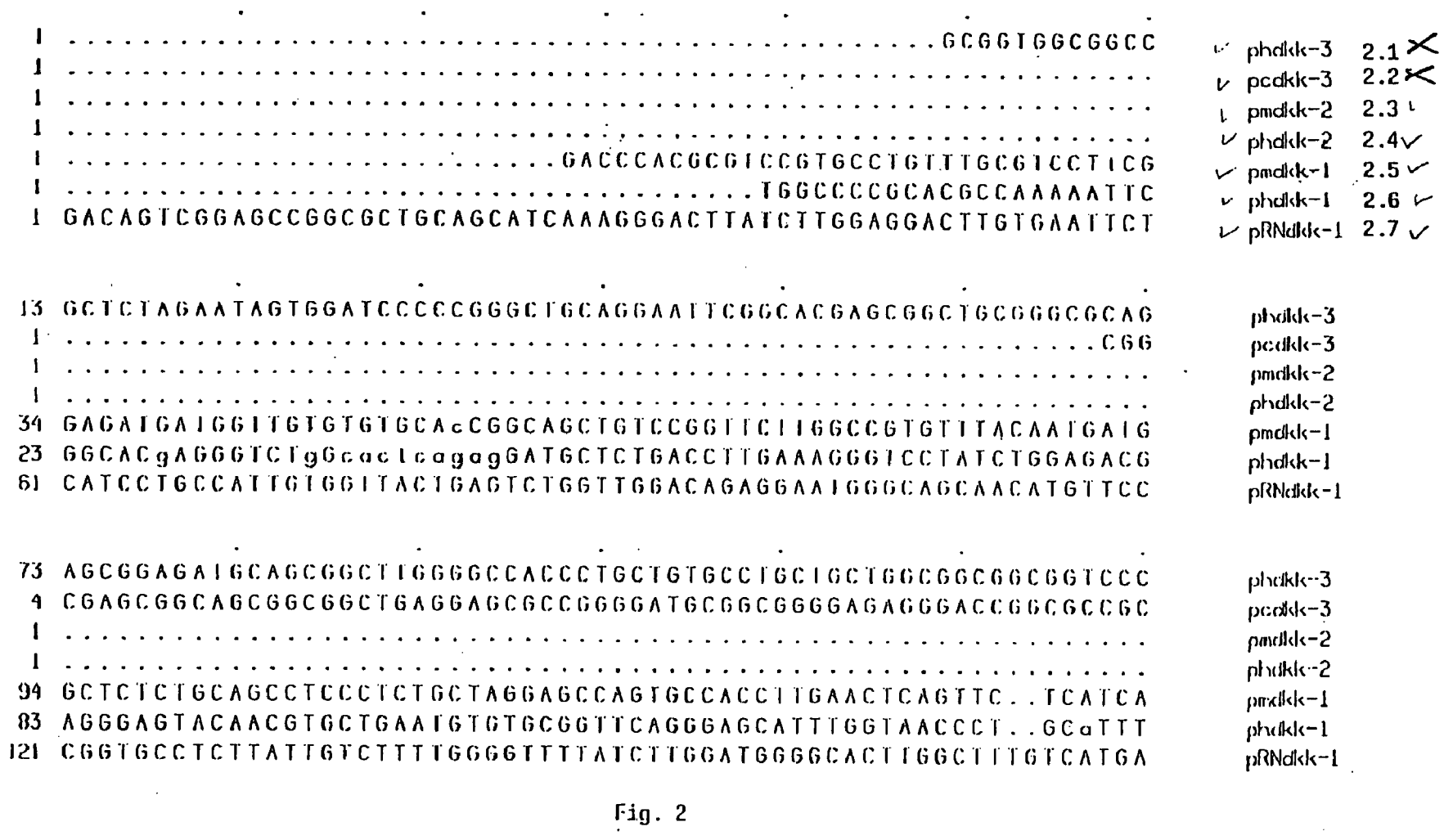
Figure 2:
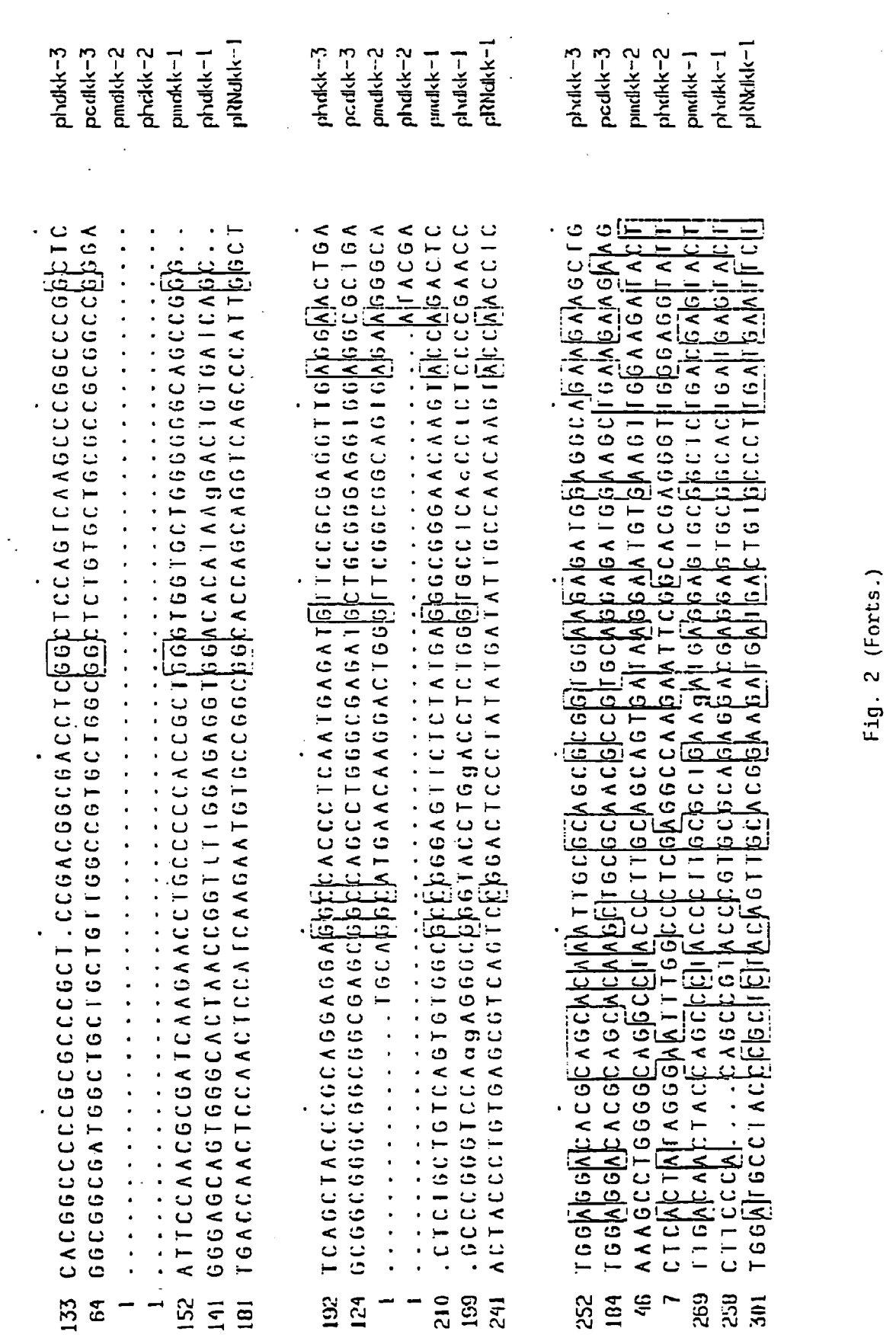
Figure 2:
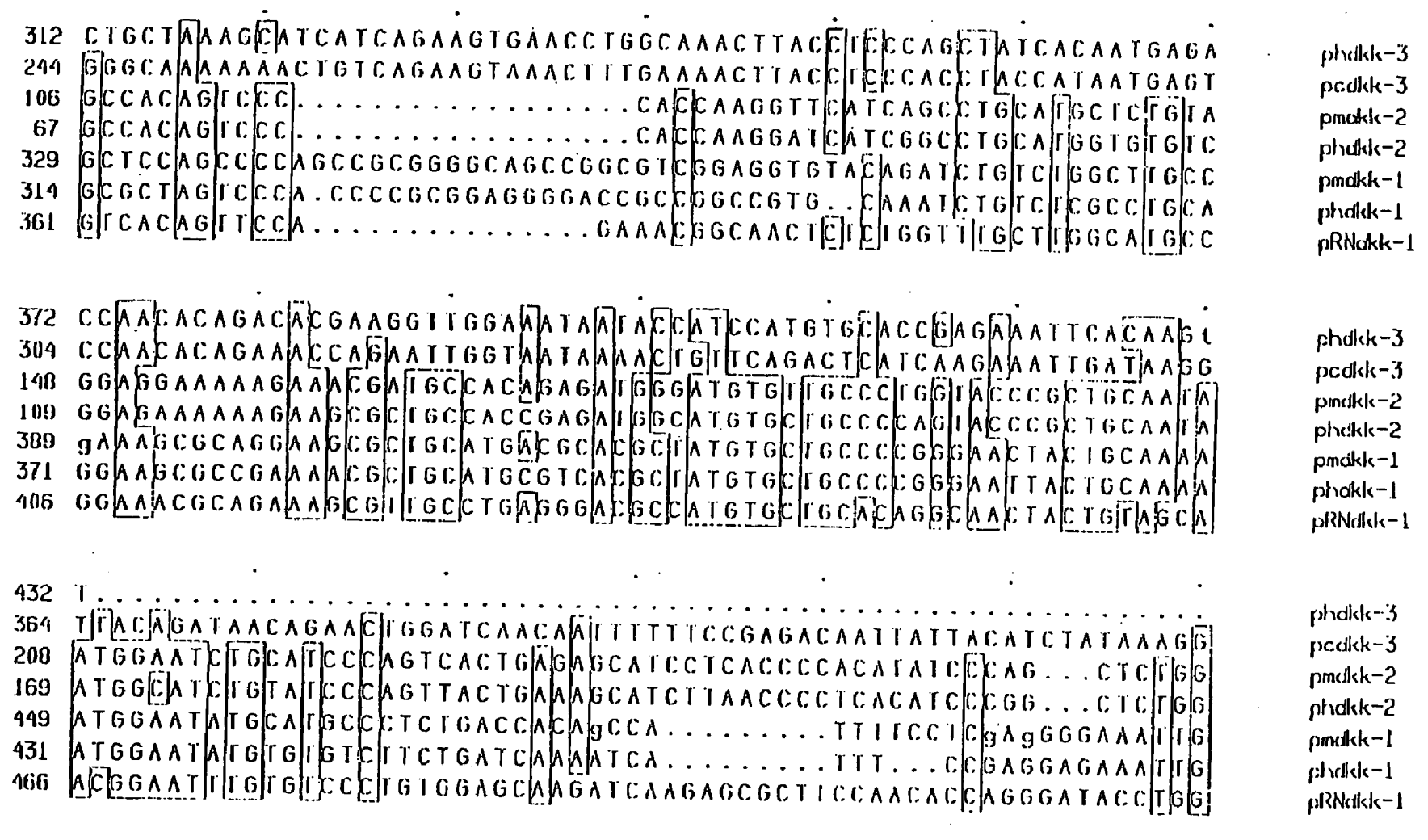
Figure 2:
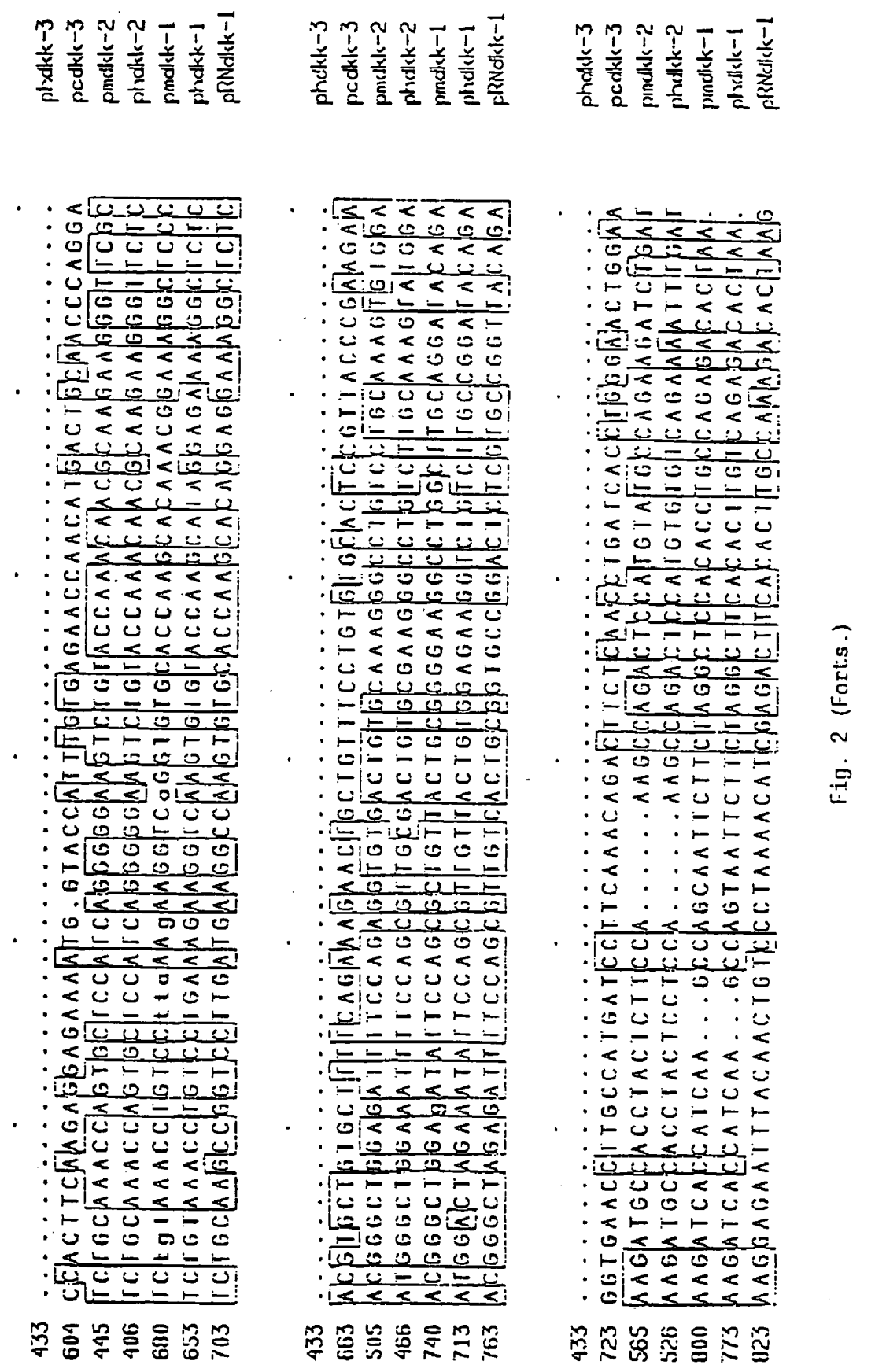
Figure 2:
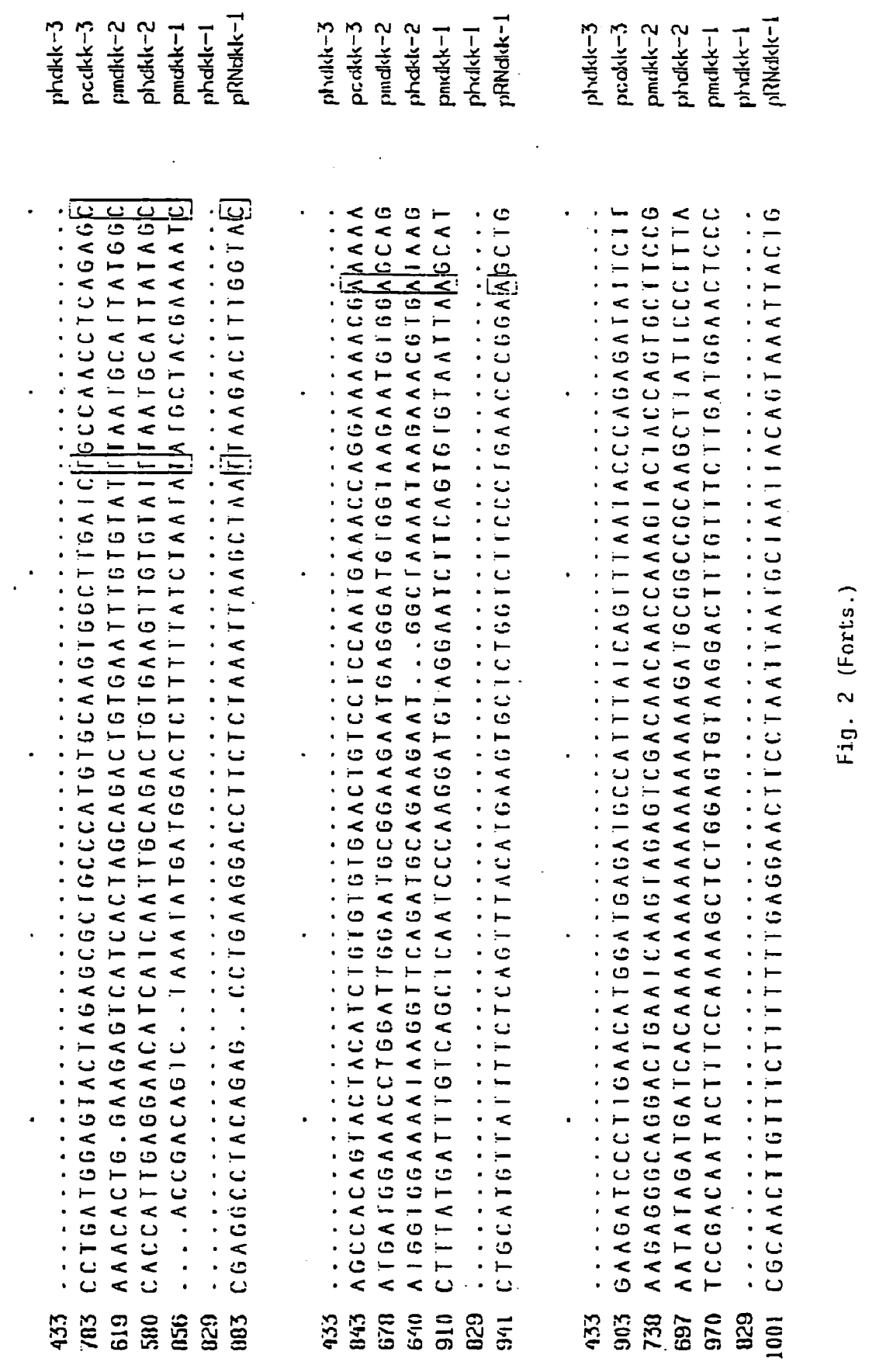

For the preparation of a (wnt-I) according to the invention, the DNA of FIG. 2.6 (SEQ ID NO: 5), phdkk-1, was provided with Bam HI linkers, then cleaved by Bam HI and inserted in the expression vector pQE-8 (Diagen) cleaved by Bam HI. The expression plasmid pQ/wnt-I was obtained. Such a plasmid codes for a fusion protein comprising 6 histidine residues (N terminus partner) and a (wnt-I) according to the invention (C terminus partner). pQ/wnt-I was used for transforming *E. coli* SG 13009 (cf. Gottesman, S. et al., J. Bacteriol. 148, (1981), 265–273). The bacteria were cultured in an LB broth with 100 µg/ml ampicillin and 25 µg/ml kanamycin, and induced with 60 µM isopropyl-β-D-thiogalactopyranoside (IPTG) for 4 h. Lysis of the bacteria was achieved by the addition of 6 M guanidine hydrochloride. Thereafter, chromatography (Ni-NTA resin) was carried out with the lysate in the presence of 8 M urea in accordance with the instructions from the manufacturer (Diagen company) of the chromatography material. The bound fusion protein was eluted in a buffer having a pH of 3.5 After its neutralization, the fusion protein was subjected to 18% SDS polyacrylamide gel electrophoresis and dyed with coomassie blue (cf. Thomas, J. O. and Kornberg, R. D., J. Mol. Biol. 149 (1975), 709–733).

It showed that a (fusion) protein according to the invention can be prepared in highly pure form.

Example 2

Preparation and Detection of an Antibody According to the Invention

A fusion protein of Example 1 according to the invention was subjected to 18% SDS polyacrylamide gel electrophoresis. After dyeing the gel with 4 M sodium acetate, an about 40 kD band was cut out of the gel and incubated in phosphate-buffered salt solution. Gel pieces were sedimented before the protein concentration of the supernatant was determined by SDS polyacrylamide gel electrophoresis which was followed by coomassie blue staining. Animals were immunized with the gel-purified fusion protein as follows:

Immunization Protocol for Polyclonal Antibodies in Rabbits

35 μg of gel-purified fusion protein in 0.7 ml PBS and 0.7 ml of complete Freund's adjuvant and incomplete Freund's adjuvant, respectively, were used per immunization.
Day 0: $1^{st}$ immunization (complete Freund's adjuvant)
Day 14: $2^{nd}$ immunization (incomplete Freund's adjuvant; icFA)
Day 28: $3^{rd}$ immunization (icFA)
Day 56: $4^{th}$ immunization (icFA)
Day 80: bleeding to death.

The rabbit serum was tested in an immunoblot. For this purpose, a fusion protein of Example 1 according to the invention was subjected to SDS polyacrylamide gel electrophoresis and transferred to a nitrocellulose filter (cf. Khyse-Andersen, J., J. Biochem. Biophys. Meth. 10, (1984), 203–209). The Western blot analysis was carried out as described in Bock, C.-T. et al., Virus Genes 8, (1994), 215–229. For this purpose, the nitrocellulose filter was incubated with a first antibody at 37° C. for one hour. This antibody was the rabbit serum (1:10000 in PBS). After several wash steps using PBS, the nitrocellulose filter was incubated with a second antibody. This antibody was an alkaline phosphatase-coupled monoclonal goat anti-rabbit IgG antibody (Dianova company) (1:5000) in PBS. 30 minutes of incubation at 37° C. were followed by several wash steps using PBS and then by the alkaline phosphatase detection reaction with developer solution (36 μM 5'-bromo-4-chloro-3-indolyl phosphate, 400 μM nitroblue tetrazolium, 100 mM Tris-HCl, pH 9.5, 100 mM NaCl, 5 mM $MgCl_2$) at room temperature, until bands were visible.

It showed that polyclonal antibodies according to the invention can be prepared.

Immunization Protocol for Polyclonal Antibodies in Chickens

40 μg of gel-purified fusion protein in 0.8 ml PBS and 0.8 ml of complete Freund's adjuvant and incomplete Freund's adjuvant, respectively, were used per immunization.
Day 0: $1^{st}$ immunization (complete Freund's adjuvant)
Day 28: $2^{nd}$ immunization (incomplete Freund's adjuvant; icFA).
Day 50: $3^{rd}$ immunization (icFA).

Antibodies were extracted from egg yolk and tested in a Western blot. Polyclonal antibodies according to the invention were detected.

Immunization Protocol for Monoclonal Antibodies in Mice

12 μg of gel-purified fusion protein in 0.25 ml PBS and 0.25 ml of complete Freund's adjuvant and incomplete Freund's adjuvant, respectively, were used per immunization. The fusion protein was dissolved in 0.5 ml (without adjuvant) in the $4^{th}$ immunization.
Day 0: $1^{st}$ immunization (complete Freund's adjuvant)
Day 28: $2^{nd}$ immunization (incomplete Freund's adjuvant; icFA)
Day 56: $3^{rd}$ immunization (icFA)
Day 84: 4th immunization (PBS)
Day 87: fusion.

Supernatants of hybridomas were tested in a Western blot. Monoclonal antibodies according to the invention were detected.

TABLE 1

Expression of DNAs according to the invention in mouse embryos

| | Dkk-1 | Dkk-2 | Dkk-3 |
|---|---|---|---|
| Neuroepithelium | | | |
| E9.5 diencephalon E12.5 | +++ ventral telencephalon M/mantle | +++ medial hypothalamus | + medial telencephalon M/ventricular zone |
| Eye | pigmented epithelium | choroid | retina |
| Spinal cord | −/+ | − | ventricular zone Roof plate |
| Mesoderm: | | | |
| Heart E10 | bulbis cordis Endocardium septum transversum | endothelium | myocardium |
| Heart E12 Blood vessels | endocardial cushion +++ aorta | endothelium +++ pulmonary artery | endocard. cushion +++ aorta + pulmonary artery |

TABLE 1-continued

Expression of DNAs according to the invention in mouse embryos

|  | Dkk-1 | Dkk-2 | Dkk-3 |
|---|---|---|---|
| Limbbud mesemchyme | E9 S | I | D |
| Bone E12 | perichondrium | S/mesenchyme | perichondrium I/mesenchyme |
| Bone E15 | Ossification centers | – | – |
| Urogenital | nephric duct S-shaped body Comma shaped body | metanephric mesenchyme | – |
| Palate | +++ | ++ | + |
| Hair follicle | +++ mesenchyme + epithelium | + | + |
| Tooth mesenchyme | – | – | +++ |
| Trunk mesoderm | +/– | +++ | ++ |

Legend:
Mesoderm: (D) deep, (I) intermediate, (L) lateral, (M) medial, (S) superficial
Intensity of expression: (–) absence, (+/–) very weak expression, (+) medium, (++) strong (+++) very strong.

The invention claimed is:

1. An isolated antibody that binds a wnt signal path inhibitor protein, wherein said wnt signal path inhibitor protein comprises the amino acid sequence of SEQ ID NO: 8 or SEQ ID NO: 9.

2. The antibody of claim 1, wherein said wnt signal path inhibitor protein comprises the amino acid sequence of SEQ ID NO: 8.

3. The antibody of claim 1, wherein said wnt signal path inhibitor protein comprises the amino acid sequence of SEQ ID NO: 9.

4. The antibody of claim 1, wherein said wnt signal path inhibitor protein is part of a fusion protein.

5. The antibody of 1, wherein said antibody is a polyclonal antibody or a monoclonal antibody.

* * * * *